United States Patent [19]
de Haan et al.

[11] Patent Number: 6,063,403
[45] Date of Patent: May 16, 2000

[54] COMPRESSED DRY-GRANULATION DESOGESTREL TABLETS

[75] Inventors: Pieter de Haan, Xb Oss; Carolus Paulus Thys, Heesch, both of Netherlands

[73] Assignee: Akzo Nobel N.V., Arnhem, Netherlands

[21] Appl. No.: 08/973,640

[22] PCT Filed: Jun. 18, 1996

[86] PCT No.: PCT/EP96/02626

§ 371 Date: Dec. 18, 1997

§ 102(e) Date: Dec. 18, 1997

[87] PCT Pub. No.: WO97/00682

PCT Pub. Date: Jan. 9, 1997

[30] Foreign Application Priority Data

Jun. 22, 1995 [EP] European Pat. Off. .............. 95201698

[51] Int. Cl.⁷ ................ A61K 9/20; A61K 9/48

[52] U.S. Cl. ............ 424/464; 424/451; 424/465; 424/489

[58] Field of Search ...................... 424/464, 465, 424/451, 489

[56] References Cited

FOREIGN PATENT DOCUMENTS 0503521  9/1992  European Pat. Off. .
WO 95/17169  6/1995  WIPO .

*Primary Examiner*—Thurman K. Page
*Assistant Examiner*—S. Howard
*Attorney, Agent, or Firm*—William M. Blackstone

[57] ABSTRACT

Compressed dry-granulation tablets or granules comprising desogestrel and the method for making them comprising compressing a composition comprising desogestrel by applying elevated pressure, followed by crushing the product of compression into particles and, thereafter, processing the particles into tablets or filling them into capsules.

7 Claims, No Drawings

COMPRESSED DRY-GRANULATION DESOGESTREL TABLETS

The invention concerns compressed dry-granulation tablets comprising desogestrel and a method of production thereof.

Desogestrel is a contraceptive steroid, widely used in preparations under various trade names among which Desogen®, Marvelon®, Mercilon®, and Gracial®.

It was observed that desogestrel shows a tendency to transfer out of tablets and granules. This is of particular concern when the tablet cores or granules comprise very low dosages of desogestrel. Tablets having desogestrel as active ingredient comprise usually 25–150 µg, and typically 25, 50, 75, 100, or 150 µg of desogestrel. For desogestrel, which has been used as active ingredient in contraceptive or HRT (hormone replacement therapy) drugs, this is not acceptable in view of its safety and reliability. For example a loss of 10% of the active substance within the shelf-life would have a dramatic effect on the amount of active ingredient in the tablet, and could lead to a tablet having less than the treshold amount of active ingredient to exert full activity.

It has now been found that compression of a dry-mix comprising desogestrel can be used for preventing the transfer of desogestrel from the tablet or granule to the environment. Apart from desogestrel the tablet or granule can further comprise an estrogen.

Examples of estrogens include ethinyl estradiol, β-estradiol, mestranol (17α-ethinyl estradiol 3-methyl ether), estrone, estradiol, estradiol valerate, and other compounds with estrogenic activity. Ethinyl estradiol and β-estradiol are the preferred estrogen.

As used herein "transfer" includes any process in which desogestrel prematurely leaves the dosage unit.

The term "dosage unit" generally refers to physically discrete units suitable as unitary dosages for humans or animals, each containing a predetermined quantity of active material (desogestrel and/or estrogen) calculated to produce the desired effect. Examples of such dosage units are tablets, granulates, powders, and pills.

Methods and compositions for making various dosage units are known to those skilled in the art. For example, methods and compositions for making, tablets and pills have been described in Remington's (18th edition, A. R. Gennaro Ed., Mack Publishing Co. Easton, Pa., 1990), at pages 1633 through 1665.

The concentration of steroid or steroids included in the tableting, mixture, and eventually the dosage unit, will of course depend on its intended use, and the eventual mass of the dosage unit. The amount of desogestrel used in a dosage unit will be well known to those skilled in the art.

A tablet core or granule according to the invention comprises typically a diluent and optionally a binder. Preferably the tablet core or granulate will also include a disintegrating agent.

Diluents or "filler excipients" are agents added to dosage units to increase the granules' and resulting dosage units' bulk, and to improve dry-binding characteristics. The preferred diluent for use in this regard is lactose. Other diluents include mannitol, sorbitol, (spray dried) lactose, (microcrystalline) cellulose, ethyl cellulose, xylitol, amylose, starch, starch-derivatives, dextrose, fructose, calcium carbonate, calcium phosphate, $NaCaPO_4$, sucrose, and mixtures thereof. The diluent will typically make up from 70 to 95% by weight of the resulting steroid loaded granules.

Binders are agents used to impart cohesive properties to the granules and tablets, resulting in more physically stable dosage units, and include hydroxypropylcellulose, amylopectin, starch, povidone (polyvinylpyrrolidone), hydroxypropylmethylcellulose, gelatin, polyethyleneglycols, ethyl cellulose, acacia gum, gelatin, glycerol, and starch based binders. The preferred binder for use with the invention is polyvinylpyrrolidone. The binder will typically make up from 0.5 to 20% by weight of the resulting, steroid loaded tablet cores or granules, and preferably 0.5 to 5% by weight.

Disintegrating agents or "disintegrators" are substances or mixtures of substances added to a tablet to facilitate its break-up or disintegration after administration. Typically such agents are modified or unmodified starches, clays, cross-linked PVP, modified or unmodified celluloses, gums or algins. The presently most preferred agents are corn starch, potato starch, wheat starch, and modified starch. Disintegrators will typically make up from 5 to 50%, preferably 5 to 15%, by weight of the resulting tableting mixture.

There is a need for a simple method of production, which does not require wet-granulation with organic solvents or water and do not require an additional drying step. The present invention concerns such method and provides compressed tablets or granules comprising desogestrel. More specifically the invention concerns a method of production of a granule, capsule or tablet comprising desogestrel, optionally together with other active compounds and/or excipients, whereby in a first step of the process the desogestrel, optionally together with other active compounds and/or excipients is mixed and subsequently compressed by applying elevated pressure, and thereafter in a second step is crushed into particles, after which in a third step the particles after admixing with lubricant may be processed into tablets or filled into capsules, using methods known in the art.

The present method is less expensive than the prior art methods, which comprise a separate granulation step, organic solvents or water, or more expensive excipients, and a drying step. The present method, moreover, can easily be scaled up. Further, no organic solvents are used, which provides a process with minimum environmental problems, whereas the particles have improved stability.

In most instances it is not necessary to use lubricants, but to prevent sticking of the desogestrel and/or estrogen powder to the rollers during roller compression small amounts of lubricant, preferably magnesium stearate, stearic acid, hydrogenated castor oil, talc, or mixtures thereof, in an amount between 2 and 0.01% w/w, and preferably about 0.25% w/w, can be added to the powder.

The powder, and optionally the lubricant (e.g. magnesium stearate or stearic acid) are compressed, preferably by using, slugging, or roller compaction. This first step of the method is a dry granulation step in which no solvents are used and wherein the powder comprising desogestrel is granulated into particles. In the present method a plate or disk of desogestrel, estrogen and excipient is obtained after compression, which is optionally crushed into irregular particles (granules). As an additional step the granulate may be sieved into desired particles and into fines. The fines may then be recirculated into the hopper of the roller compactor or the tabletting machine.

During the compression the applied pressure is an important parameter. By applying pressure the temperature between the rollers increases. An increase of the roller compaction pressure results in higher strength of the compacted plate resulting in a low friability. Furthermore, the production yield increases with the pressure. Suitable compaction pressures to give low friability and degradation, and high production yields, are between about 0.5 and 500 MPa (megaPascal). A preferred pressure is about 200–400 MPa, giving a minimum activity loss and maximum yield.

The compactor can be any compactor, being for instance concave or convex, having straight or profilated rollers or different design of powder transport screws. The Alexander WP120 roller compactor appears to be a convenient compactor.

Usually the compacted powder has to be crushed into smaller particles. This crushing step is important for the particle size distribution, which depends on the crushing method used. In principle any crusher can be used, for instance a pyramid or a roller crusher, preferably together with a crushing sieve of the Alexander Roller Compactor, with a Comil conical granulator, or with a Frewitt crushing sieve. Using, this type of sieves, generally a production yield of about 50% is easily obtainable. The fines that cannot be used are sieved out and can be recirculated to the compression step.

A preferred embodiment is slugging, in which slugs or large tablets are compressed using heavy duty tablet compacting equipment and subsequently are ground to the desired granulation characteristics.

The granules can be tabletted or capsulated, for instance in hard gel capsules, such as gelatin capsules.

According to the above-mentioned methods tablets comprising desogestrel were made having the following contents:

|  | Tablet A mg | Tablet B mg | Tablet C mg |
|---|---|---|---|
| desogestrel | 0.150 | 0.150 | 0.150 |
| ethinyl estradiol | 0.030 | 0.030 | 0.030 |
| sodium starch glycolate | 1.30 | 1.30 | 1.20 |
| stearic acid | 1.30 | 1.30 | — |
| mannitol qsad | 65.0 | 65.0 | — |
| magnesium stearate | — | — | 0.30 |
| Pharmatose DCL-11qsad | — | — | 60.0 |

Tablets A according to this invention were prepared by pre-mixing desogestrel and EE in a Turbula Mixer with approx. 10% of the mannitol and screening the mixture using a 250 µm sieve. The screened mass was mixed with the rest of the mannitol and sodium starch glycolate and subsequently with 1.5% of stearic acid (<250 µm) in a Lödige mixer. Compacts were slugged at 340 MPa. After crushing the slugs, the dry granules smaller than 710 µm were collected and mixed in a Turbula mixer with 0.5% of stearic acid. This mixture was compressed on a Korsch PH-106 tabletting machine to tablets with a weight of 65 mg.

Tablets B (prior art tablets) were obtained by pre-mixing desogestrel and EE in a Turbula Mixer with approx. 10% of the mannitol and screening the mixture using a 250 µm sieve. The screened mass was mixed with the rest of the mannitol and sodium starch glycolate and subsequently with 1.5% of stearic acid (<250 µm) In a Lödige mixer. Mixing was proceeded in a Turbula mixer with 0.5% of stearic acid. This mixture was compressed on a Korsch PH-106 tabletting machine to tablets with a weight of 65 mg.

Tablets C (prior art tablets) were obtained by mixing desogestrel and EE with spray dried lactose (Pharmatose DCL-11) in a Gral High Shear Mixer. Thereafter the other excipients were also mixed in the mixture and thereafter directly compressed to tablets with a weight of 60 mg.

Sublimation properties of tablet A (according to the invention) were compared with those of prior art tablets B and C. Samples were stored for 72 h at 70° C. at a pressure of 15 kPa. Sublimation vapours were collected on a cold finger at 4° C. and the amount of desogestrel sublimed was analysed quantitatively:

| Amount of desogestrel sublimed (% of quantity in starting tablet) | | |
|---|---|---|
| A | B | C |
| 9.0 | 12.3 | 15.2 |

The tablets according to the invention (A) showed improved properties towards sublimation compared with prior art tablets B and C, and are therefore anticipated to have improved shelf-life.

What is claimed is:

1. A method of producing compressed dry-granulation tablets, capsules or granules comprising desogestrel, said method comprising:
    a) compressing material comprising desogestrel by applying elevated pressure to produce compressed material;
    b) crushing the compressed material produced in step a) to produce particles; and
    c) processing the particles produced in step b) into tablets, capsules, or granules.

2. The method of claim 1 wherein the material of step a) is dry compressed material.

3. The method of claim 1 wherein the material of step a) further comprises at least one of an additional active compound and an excipient.

4. The method of claim 1 wherein the material comprising desogestrel is compressed by means of roller compaction or slugging.

5. The method of claim 1 wherein the elevated pressure is between about 0.5 and about 500 MPa.

6. The method of claim 5 wherein the elevated pressure is between about 200 and about 400 MPa.

7. Compressed dry-granulation tablets, capsules or granules made by the method of claim 1.

* * * * *